(12) United States Patent
Le Berre et al.

(10) Patent No.: US 9,598,342 B2
(45) Date of Patent: Mar. 21, 2017

(54) PRODUCTION OF ACETIC ACID WITH ENHANCED CATALYST STABILITY

(71) Applicant: Celanese International Corporation, Irving, TX (US)

(72) Inventors: Carole Marie Le Berre, Lacroix-Falgrade (FR); Duc Hahn Nguyen, Marseille (FR); Philippe Gilles Serp, Clermont Lefort (FR); Philippe Kalck, Auzeville Tolosane (FR); G. Paull Torrence, League City, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 73 days.

(21) Appl. No.: 14/211,522

(22) Filed: Mar. 14, 2014

(65) Prior Publication Data

US 2014/0309455 A1    Oct. 16, 2014

Related U.S. Application Data

(60) Provisional application No. 61/789,446, filed on Mar. 15, 2013.

(51) Int. Cl.
*C07C 229/00* (2006.01)
*C07C 51/12* (2006.01)

(52) U.S. Cl.
CPC .................... *C07C 51/12* (2013.01)

(58) Field of Classification Search
CPC .................................. C07C 229/00
USPC .......................................... 562/519
See application file for complete search history.

(56) References Cited

U.S. PATENT DOCUMENTS

| | | | |
|---|---|---|---|
| 3,769,329 A | 10/1973 | Knox et al. | |
| 4,433,166 A | 2/1984 | Singleton et al. | |
| 5,001,259 A | 3/1991 | Smith et al. | |
| 5,026,908 A | 6/1991 | Smith et al. | |
| 5,144,068 A | 9/1992 | Smith et al. | |
| 5,442,107 A | 8/1995 | Beevor et al. | |
| RE35,377 E | 11/1996 | Steinberg et al. | |
| 6,677,480 B2 | 1/2004 | Huckman et al. | |
| 7,005,541 B2 * | 2/2006 | Cheung et al. | 562/519 |
| 7,053,241 B1 | 5/2006 | Torrence | |
| 7,115,774 B2 | 10/2006 | Magna et al. | |
| 7,582,792 B2 | 9/2009 | Zoeller et al. | |
| 7,608,744 B1 | 10/2009 | Johnston et al. | |
| 7,678,939 B2 | 3/2010 | Torrence | |
| 7,812,191 B2 | 10/2010 | Hallinan et al. | |
| 7,842,844 B2 | 11/2010 | Atkins | |
| 7,863,489 B2 | 1/2011 | Johnston et al. | |
| 7,884,253 B2 | 2/2011 | Stites et al. | |
| 8,299,132 B2 | 10/2012 | Gracey et al. | |
| 8,299,133 B2 | 10/2012 | Gracey et al. | |
| 8,329,960 B2 | 12/2012 | Gracey et al. | |
| 8,378,153 B2 | 2/2013 | Daniel et al. | |
| 8,524,954 B2 | 9/2013 | Ditzel et al. | |
| 8,742,168 B2 * | 6/2014 | Hallinan et al. | 562/519 |
| 8,748,673 B2 | 6/2014 | Warner et al. | |
| 2010/0197985 A1 | 8/2010 | Johnston et al. | |
| 2011/0190547 A1 | 8/2011 | Jevtic et al. | |
| 2011/0190548 A1 | 8/2011 | Jevtic et al. | |
| 2011/0275862 A1 | 11/2011 | Johnston et al. | |
| 2011/0282110 A1 | 11/2011 | Johnston et al. | |
| 2012/0041075 A1 | 2/2012 | Johnston et al. | |
| 2013/0035524 A1 | 2/2013 | Orosco et al. | |

FOREIGN PATENT DOCUMENTS

| | | |
|---|---|---|
| CN | 101716527 | 6/2010 |
| EP | 0153834 | 9/1985 |
| EP | 1904426 | 4/2008 |
| EP | 2060553 | 5/2009 |
| EP | 2072486 | 6/2009 |
| EP | 2072487 | 6/2009 |
| EP | 2072488 | 6/2009 |
| EP | 2072490 | 6/2009 |
| EP | 2072492 | 6/2009 |

OTHER PUBLICATIONS

Gaub, et al., "Synthesis of Acetic Acid and Acetic Acid Anhydride from Methanol", Applied Homogeneous Catalysis with Organometallic Compounds, 1996, vol. 1, 104, 138.
J. Jones, et al., Platinum Metals Review, vol. 44, No. 3, pp. 94-104 (Jul. 2000).

* cited by examiner

*Primary Examiner* — Yong Chu
*Assistant Examiner* — Sonya Wright
(74) *Attorney, Agent, or Firm* — Kilpatrick Townsend & Stockton LLP

(57) ABSTRACT

Processes for the production of acetic acid by carbonylation of methanol and reactive derivatives thereof in a liquid phase reaction medium, wherein the reaction medium comprises a finite amount of water, a homogeneous catalyst, an alkyl halide promoter, and a catalyst stabilizer/co-promoter comprising an imidazolium cation $R_1R_2Im+$ as an iodide salt, wherein $R_1$ and $R_2$ are each independently a substituted or unsubstituted alkyl or cycloalkyl, with the proviso that $R_1$ and $R_2$ are not the same.

20 Claims, 2 Drawing Sheets

PRODUCTION OF ACETIC ACID WITH ENHANCED CATALYST STABILITY

CROSS-REFERENCE TO RELATED APPLICATIONS

This is a non-provisional application that claims priority to U.S. Provisional Application No. 61/789,446 filed on Mar. 15, 2013, the entirety of which is incorporated herein by reference.

FIELD OF THE INVENTION

The present invention relates generally to the carbonylation of methanol to produce acetic acid and, in particular, to improving catalyst stability in such processes using one or more imidazolium salts.

BACKGROUND OF THE INVENTION

A widely used and successful commercial process for synthesizing acetic acid involves the catalyzed carbonylation of methanol with carbon monoxide. The catalyst contains rhodium and/or iridium and a halogen promoter, typically methyl iodide. The reaction is conducted by continuously bubbling carbon monoxide through a liquid reaction medium in which the catalyst is dissolved. The reaction medium comprises acetic acid, methyl acetate, water, methyl iodide and the catalyst. Conventional commercial processes for the carbonylation of methanol include those described in U.S. Pat. Nos. 3,769,329, 5,001,259, 5,026,908, and 5,144,068, the entireties of which are incorporated herein by reference. Another conventional methanol carbonylation process includes the Cativa™ process, which is discussed in Jones, J. H. (2002), "*The Cativa™ Process for the Manufacture of Acetic Acid*," Platinum Metals Review, 44(3): 94-105, the entirety of which is incorporated herein by reference.

The literature describes the addition of various components to the carbonylation reaction medium in order to increase catalyst stability and/or prevent loss of the catalyst during processing steps. Imidazole salts, for example, have been utilized with some success in improving carbonylation catalyst stability. European Patent No. 0 153 834, the entirety of which is incorporated herein by reference, discloses a process for preparing acetic acid by carbonylation of a methanol feed stock in a liquid reaction medium comprising a rhodium catalyst, an iodide or bromide component, an imidazole stabilizing compound, water and acetic acid. Suitable imidazole stabilizing compounds have the general formula:

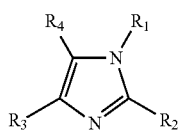

wherein $R_1$, $R_2$, $R_3$, and $R_4$ are each independently hydrogen, alkyl, aryl, cycloalkyl or alkaryl hydrocarbyl radicals.

U.S. Pat. No. 5,442,107 describes a process for preparing a carboxylic acid having (n+1) carbon atoms (e.g. acetic acid) from an alcohol having n carbon atoms (e.g. methanol) by liquid phase, rhodium catalyses carbonylation. The process is characterized by using a catalyst stabilizer selected from certain classes of imidazolium iodides, alkyl substituted pyridinium iodides and hydroxypyridinium iodides. Most preferred are those derived from the amines 2-ethyl-4-methyl imidazole, 4-ethylpyridine, 4-t-butylpyridine and 3,4-lutidine by quarternisation with a methyl group.

U.S. Pat. No. 7,115,774, the entirety of which is incorporated herein by reference, discloses a process for carbonylating alcohols with carbon monoxide in the liquid phase, wherein the process comprises a halogenated promoter in at least one non-aqueous ionic liquid comprising at least one salt of the formula $Q^+A^-$, in which $Q^+$ represents a quaternary ammonium and/or a quaternary phosphonium cation, and $A^-$ is an anion capable of forming a liquid salt below 90° C. Suitable quaternary ammonium and/or quaternary phosphonium cations include N-butylpyridinium hexafluorophosphate, N-ethyl pyridinium tetrafluoroborate, pyridinium fluorosulfonate, 3-butyl-1-methylimidazolium tetrafluoroborate, 3-butyl-1-methylimidazolium hexafluoroantimonate, 3-butyl-1-methylimidazolium hexafluorophosphate, 3-butyl-1-methylimidazolium trifluoromethylsulfonate, 3-butyl-1-methylimidazolium bis(trifluoromethylsulfonyl)amide, trimethylphenylammonium hexafluorophosphate and tetrabutylphosphonium tetrafluoroborate.

U.S. Pat. No. 7,582,792, the entirety of which is incorporated herein by reference, discloses a carbonylation process for the production of a carboxylic acid by combining in a reaction zone a carbonylation feedstock compound comprising an alkanol, a Group VIII metal carbonylation catalyst comprising rhodium (Rh), iridium (Ir), or a compound thereof; an onium salt compound comprising a 1,3-dialkylimidazolium iodide or an N-alkylpyridinium iodide; and carbon monoxide under carbonylation conditions of pressure and temperature, wherein neither hydrogen iodide nor an alkyl iodide exogenous or extraneous to the carbonylation process is added or supplied to the reaction zone.

U.S. Pat. No. 5,144,068, the entirety of which is incorporated herein by reference, discloses a process for producing acetic acid by reacting methanol with carbon monoxide in a liquid reaction medium containing a rhodium (Rh) catalyst and comprising water, acetic acid, methyl iodide, and methyl acetate, wherein catalyst stability is maintained in the reaction by maintaining in said reaction medium during the course of said reaction about 0.1 wt. % to less than 14 wt. % of water together with (a) an effective amount in the range of about 2 wt. % to 20 wt. % of a catalyst stabilizer selected from the group consisting of iodide salts which are soluble in said reaction medium in effective concentration at reaction temperature, (b) about 5 wt. % to 20 wt. % of methyl iodide, and (c) about 0.5 wt. % to 30 wt. % of methyl acetate. Suitable iodide salts may be a quaternary iodide salt or an iodide salt of a member of the group consisting of the metals of Group IA and Group IIA of the Periodic Table.

U.S. Pat. No. 7,005,541, the entirety of which is incorporated herein by reference, discloses a process for producing acetic acid by carbonylation of methanol in a reaction medium having low water content whereby carbon monoxide is reacted with methanol in the presence of a catalyst system comprising a Group VIII metal catalyst, namely rhodium (Rh), iridium (Ir), cobalt (Co), nickel (Ni), ruthenium (Ru), palladium (Pd) or platinum (Pt), a halogen promoter (i.e. an alkyl iodide such as methyl iodide), and a stabilizer/co-promoter. The catalyst system is dissolved in a liquid medium comprising methyl acetate, acetic acid, a finite amount of water (e.g., at least about 0.1 wt. %) and any other compatible solvent. The stabilizer/co-promoter of the catalyst system may be in the form of a soluble salt from an alkali metal, an alkaline earth metal or a quaternary ammonium or phosphonium salt, particularly an iodide or acetate salt, which generates an effective amount of iodide ions in the reaction medium. The amount of iodide present in the reaction medium is between about 2 and 20 wt. %, and the concentration of alkyl iodide (i.e. methyl iodide) in the reaction medium is between about 2 and 30 wt. %. Suitable catalyst stabilizers or co-promoters include lithium iodide, lithium acetate or mixtures thereof.

U.S. Pat. No. 7,678,939, the entirety of which is incorporated herein by reference, discloses a process for producing acetic acid by carbonylation of methanol wherein catalyst stability is achieved by maintaining, in the reaction medium, a rhodium-based catalyst system having a halogen promoter and an iodide salt co-promoter wherein the iodide salt co-promoter has an iodide concentration of greater than about 3 wt. %. Suitable iodide salt co-promoters include a soluble salt of an alkali metal or alkaline earth metal or a quaternary ammonium or phosphonium salt. At least one ruthenium catalyst stabilizer, at least one tin catalyst stabilizer, or mixtures thereof are also incorporated into the catalyst system. The water concentration of the reaction medium is between 0.1 to 14 wt. %.

Chinese Publication CN101716527A discloses a high-stability catalyst for producing acetic acid by low pressure carbonylation. The catalyst uses rhodium as a main catalyst, uses methyl iodide or the mixture of the methyl iodide and lithium iodide as a cocatalyst and uses an ionic liquid as a stabilizer. The ionic liquid stabilizer is 1,3-dialkyl imidazole phosphatic dialkyl ester ([RR'Im] [DRP]), wherein R and R' are alkyl groups in which the number of carbon atoms is within 1-5, and R and R' can be both same and different. The ionic liquid is used as the efficient stabilizer, and the mixture of the acetic acid, methyl acetate and water is used as a reaction medium. It is reported that the stabilizer can enable the rhodium catalyst to keep high stability under very low water content, but the stability of a traditional Monsanto catalyst can be ensured only by maintaining high water content in a reaction system.

Imidazoles have also been used in extracting acetic acid. U.S. Pat. No. 7,812,191, for example, describes a method for removing hydrocarbon impurities from acetic acid. The method comprises extracting acetic acid with a hydrophilic imidazolium salt. The imidazolium salt preferably has the general structure of

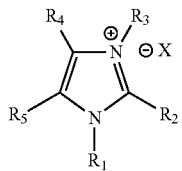

wherein $X_8$ is a counter ion and $R_1$, $R_2$, $R_3$, $R_4$, and $R_5$ are independently selected from the group consisting of $C_1$-$C_6$ hydrocarbon substitutes. The method is useful for removing hydrocarbon impurities from the alkane distillation bottoms stream of a methanol carbonylation process.

As reflected above, various processes exist for the production of acetic acid utilizing a catalyst system comprising, for example, a Group VIII metal catalyst, such as a rhodium-based catalyst, in conjunction with a halogen promoter and/or stabilizer. The need remains for novel processes for producing acetic acid with improved catalyst stability.

SUMMARY OF THE INVENTION

In a first embodiment, the present invention is directed to a process for producing acetic acid, the process comprising the steps of: reacting carbon monoxide with at least one reactant selected from the group consisting of methanol, methyl acetate, methyl formate, dimethyl ether and mixtures thereof in a reactor containing a reaction medium to produce a reaction product comprising acetic acid, wherein the reaction medium comprises a finite amount of water, optionally from 0.1 wt. % to 8 wt. %, a homogeneous catalyst, optionally comprising iridium or rhodium, an alkyl halide promoter, optionally a metal iodide salt, and a catalyst stabilizer comprising an imidazolium cation $R_1R_2Im^+$ as an iodide salt, wherein $R_1$ and $R_2$ are each independently a substituted or unsubstituted alkyl or cycloalkyl, with the proviso that $R_1$ and $R_2$ are not the same; and maintaining the reaction medium at a total iodide ion concentration of from 2 to 35 wt. %, e.g., from 3 to 35 wt. %, and an alkyl halide promoter concentration of greater than 1 wt. %, based on the total weight of the reaction medium.

The catalyst stabilizer preferably has a melting point less than 170° C. and may be a liquid at 25° C. $R_1$ preferably is selected from ethyl, butyl, hexyl and octyl and $R_2$ preferably is methyl. In some preferred aspects, the catalyst stabilizer comprises butyl methyl imidazolium ion, hexyl methyl imidazolium ion, or octyl methyl imidazolium ion.

The imidazolium cation optionally is maintained in the reaction medium at a concentration of from 1.5 wt. % to 28 wt. %, based on the total weight of the reaction medium. The process preferably has a carbonylation rate from 10 to 40 mol/l/hr, e.g., from 15 to 25 mol/l/hr. The reaction medium ideally is maintained at a total iodide ion to catalyst molar ratio of from 25:1 to 950:1. The reaction medium may further comprise an alkali or alkaline earth metal iodide salt at an imidazolium to alkali or alkaline earth metal molar ratio of from 1:10 to 10:1. Preferably at least 99% of the homogeneous catalyst remains solubilized in the reaction medium when cooled to at least 20° C. The alkyl halide promoter optionally is maintained in the reaction medium at a concentration greater than 5 wt. %. The reaction medium may further comprise methyl acetate, in which case the process preferably further comprises the step of maintaining the reaction medium at a methyl acetate concentration from 0.5 to 20 wt. %, e.g., from 0.5 to 10 wt. %, based on the total weight of the reaction medium.

BRIEF DESCRIPTION OF THE DRAWING

The present invention will be better understood in view of the appended non-limiting figures, in which.

DETAILED DESCRIPTION OF THE INVENTION

Introduction

Figure 1:
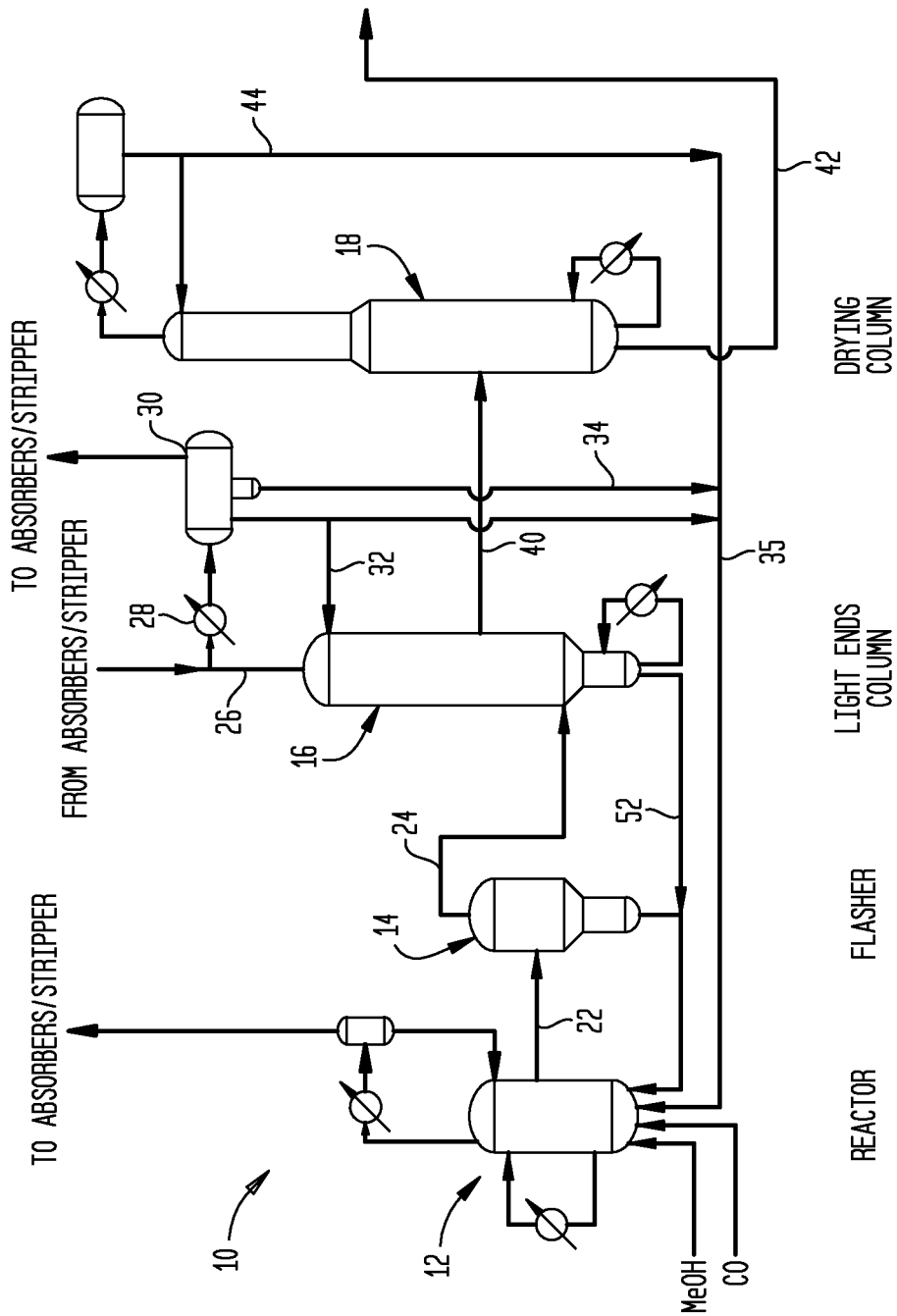
FIG. 1 illustrates an exemplary carbonylation system according to one embodiment of the invention.

It has now surprisingly and unexpectedly been discovered that catalyst stability in a carbonylation process for producing acetic acid can be significantly improved by including in the carbonylation reactor medium certain imidazolium cations as iodide salts, optionally in combination with one or more inorganic iodide salt(s) (e.g., lithium iodide, sodium iodide or potassium iodide).

The present invention therefore relates to a carbonylation process for forming acetic acid. The process comprises reacting carbon monoxide with at least one reactant selected from the group consisting of methanol, methyl acetate, methyl formate, dimethyl ether and mixtures thereof in a reactor containing a reaction medium to produce a reaction product comprising acetic acid. The reaction medium comprises a finite amount of water, a homogeneous catalyst, an alkyl halide promoter, optionally methyl acetate, and a catalyst stabilizer comprising an imidazolium cation $R_1R_2Im^+$ as an iodide salt, wherein $R_1$ and $R_2$ are each independently a substituted or unsubstituted alkyl or cycloalkyl, with the proviso that $R_1$ and $R_2$ are not the same. The reaction medium is maintained at a total iodide ion concentration of from 2 to 35 wt. % and at an alkyl halide promoter concentration of greater than 1 wt. %, based on the total weight of the reaction medium. It has now been discovered that employing imidazolium catalyst stabilizers of the type specified in the reaction medium specified surprisingly and unexpectedly reduces catalyst precipitation, thereby improving overall catalyst stability.

Carbonylation Processes

The carbonylation processes of the invention preferably occur in the presence of a finite amount of water, optionally at water concentrations from 0.1 wt. % to 14 wt. % of the reaction medium in which the carbonylation reaction takes place. Furthermore, the processes described herein relate to carbonylation reactions catalyzed by a rhodium-based or iridium-based catalyst system in the presence of a halogen catalyst promoter, optionally elemental iodine ($I_2$), hydrogen iodide (HI) or an organic iodide such as methyl iodide, and one or more stabilizers, which provide an iodide ion concentration equivalent to greater than 2 wt. %, optionally greater than 3 wt. %, in the reaction medium. According to the present invention, the one or more stabilizers include at least one imidazolium cation as an iodide salt, and in particular an imidazolium cation of formula $R_1R_2Im^+$ as an iodide salt, The imidazolium iodide salt advantageously stabilizes the iridium or rhodium-based catalyst systems incorporating the halogen promoter. In one optional embodiment, the one or more iodide salts includes the imidazolium salt in combination with an inorganic iodide salt co-promoter, such as lithium, sodium or potassium iodide.

An important aspect of the processes described herein is the surprising and unexpected discovery that carbonylation catalyst stability may be advantageously enhanced by incorporating the aforementioned imidazolium cations into the reaction medium, which optionally may be used in combination with an inorganic iodide co-promoter, such as lithium iodide, preferably in a low water carbonylation environment. The use of the particular imidazolium cations also advantageously does not appreciably reduce carbonylation rates. In some embodiments, for example, the carbonylation rate may be at least 15.0 mol/l/hr, e.g., at least 15.5 mol/l/hr, at least 16.0 mol/l/hr, at least 17.0 or at least 18.0 mol/l/hr. In terms of ranges, the carbonylation rate optionally ranges from 10.0 to 40.0 mol/l/hr, from 15.0 to 25.0 mol/l/hr, from 16.0 to 25.0 mol/l/hr, from 17.0 to 25.0 mol/l/hr, or from 18.0 to 25.0 mol/l/hr.

The catalyst stabilizer added to the reaction system may comprise an imidazolium cation of the formula: $R_1R_2Im^+$ as a halide (i.e., iodide, chloride), hydroxide or carboxylate salt, e.g., acetate salt. As used herein, "Im" refers to an imidazolium ring containing two nitrogen bonds. Thus, the cation $R_1R_2Im^+$ refers to an imidazolium cation of the following structure.

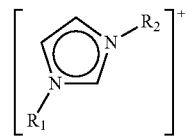

As indicated above, $R_1$ and $R_2$ are each independently a substituted or unsubstituted alkyl or cycloalkyl, with the proviso that $R_1$ and $R_2$ are not the same. Illustrative examples of suitable alkyl groups include methyl, ethyl, propyl, butyl, pentyl, hexyl, heptyl, octyl, nonyl, decyl, dodecyl, tetradecyl, and hexadecyl. Exemplary cycloalkyl groups include, but are not limited to, cyclopentyl and cyclohexyl groups. In some embodiments, $R_1$ and $R_2$ may be substituted compounds. Illustrative examples of suitable substituents include, but are not limited to, hydroxyl groups and halides. Preferably, the imidazolium cation does not include any aromatic substituents, e.g., is free of phenyl groups, as the presence of such moieties may enhance rhodium carbonyl complex crystallization leading to reduced catalyst activity.

In certain embodiments, the water concentrations in the reaction mediums in the processes described herein are maintained from 0.1 wt. % to 14 wt. %. More preferably, the water concentration in the reaction medium described herein is maintained from 0.1 wt. % to 8 wt. %. In other embodiments, the water concentrations in the reaction mediums in the processes described herein is maintained from 0.1 wt. % to 6 wt. %. In still other embodiments, the water concentrations in the reaction mediums in the processes described herein are maintained from 0.1 wt. % to 4 wt. %, or 0.1 wt. % to 2 wt. %.

The incorporation of at least one of the imidazolium salts in the reaction medium reduces the tendency of rhodium in the rhodium-based catalyst system to crystallize and/or precipitate out of solution during the production and purification of acetic acid. Rhodium compounds are particularly susceptible to instability leading to precipitation of the rhodium catalyst as $RhI_3$ during recovery of acetic acid, particularly in the flasher unit. Rhodium is a very expensive metal and loss of the metal through precipitation may have significant negative financial impact on commercial acetic acid production processes by affecting catalyst usage and maintenance of high production.

None of the known systems disclose the use of imidazolium cations of the type claimed herein in homogeneous carbonylation processes under low water conditions to stabilize rhodium without causing precipitation or crystallization of rhodium carbonyl complexes. The processes described herein recognize that this unique combination of carbonylation system components provides significant stability to rhodium-based homogeneous catalyst systems. In a preferred embodiment, the processes described herein relate to the use of rhodium-based catalyst systems, although they could also be employed in iridium-based catalyst systems or a system comprising both rhodium and iridium. For purposes of this disclosure, a "rhodium-based catalyst system" or "rhodium-based catalyst" means a catalyst system providing a rhodium metal concentration in a methanol carbonylation reaction medium of at least 300 wppm.

In certain embodiments, the rhodium-based catalyst systems described herein provide from 300 wppm to 5,000 wppm of rhodium in the reaction medium. In other embodiments, the rhodium-based catalyst systems described herein provide from 1,000 wppm to 4,000 wppm of rhodium in the reaction medium. In still other embodiments, the rhodium-based catalyst systems described herein provide from 2,000 wppm to 3,000 wppm of rhodium in the reaction medium. In certain embodiments, the rhodium concentration in the reaction medium is at least 1000 wppm. In other embodiments, the rhodium concentration in the reaction medium is at least 1500 wppm. In still other embodiments, the rhodium concentration in the reaction medium is at least 2000 wppm.

In addition to rhodium and/or iridium, the reaction mediums of the processes described herein also may include the use of a halogen promoter, such as elemental iodine, hydrogen iodide and/or an organic iodide and an alkali or alkaline earth metal iodide salt co-promoter, such as lithium iodide. In certain embodiments, the organic iodide is an alkyl iodide such as methyl iodide. The alkyl iodide may be maintained, for example, in the reaction medium at a concentration of from 2.0 wt. % to 30 wt. %. In other embodiments, the alkyl iodide is maintained at a concentration in the reaction medium of 5.0 wt. % to 15 wt. %. In still another embodiment, the alkyl iodide is maintained in the reaction medium at a concentration of 5.0 wt. % to 10.0 wt. %.

According to the invention, the stabilizer used in the reaction medium includes at least one imidazolium salt. In one embodiment, the imidazolium salt comprises an imidazolium iodide salt. In another embodiment, the imidazolium stabilizer comprises a imidazolium carboxylate (e.g., acetate), halide, hydroxide, or a mixture thereof.

The imidazolium salt stabilizer may be added to the reaction medium as an iodide salt or as a non-iodide salt that will generate an iodide salt in the reaction medium. In such cases, the non-iodide salt will react with HI and be converted to the corresponding imidazolium iodide salt by the following equation:

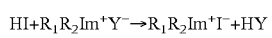

where $Y^-$ is an anion other than an iodide anion, e.g., carboxylate (optionally acetate), hydroxide or a halide other than iodide.

In addition to the imidazolium stabilizer, the process optionally may employ a co-promoter that is a soluble inorganic salt, preferably of an alkali metal, optionally lithium iodide or sodium iodide, or of an alkaline earth metal. For example, lithium iodide, lithium acetate, or a mixture thereof may be employed. The inorganic salt co-promoter may be added as a non-iodide salt that will generate an iodide salt in the reaction solution. The iodide catalyst stabilizer may be introduced directly into the reaction system. Alternatively, the iodide salt may be generated in situ since under the operating conditions of the reaction system, a wide range of non-iodide salt precursors will react with HI to generate the corresponding co-promoter iodide salt stabilizer. For additional detail regarding iodide salt generation, see U.S. Pat. No. 5,001,259 to Smith et al.; U.S. Pat. No. 5,026,908 to Smith et al.; and U.S. Pat. No. 5,144,068 also to Smith et al., the entireties of which are incorporated herein by reference.

In some embodiments, the imidazolium stabilizer may be formed in situ by adding a neutral imidazole and allowing it to quaternize with methyl iodide and/or a low level alkyl iodide impurity such as ethyl iodide or butyl iodide.

The imidazolium iodide salt is preferably maintained in the reaction medium in an amount sufficient to effectively stabilize the rhodium or iridium catalyst. The concentrations of the imidazolium iodide and optional inorganic co-promoter, e.g., LiI, are such that they maintain a total iodide ion concentration in the reaction medium of greater than 2 wt. %, optionally greater than 3 wt. %, optionally from 2 to 35 wt. %, from 3 to 35 wt. %, from 4 to 35 wt. % or from 5 to 35 wt. %. In still other embodiments, the concentration of these co-promoter(s) are such that they maintain a total iodide ion concentration in the reaction medium of from 2 to 20 wt. %, e.g., from 5 to 15 wt. %, or from 5 to 10 wt. %. In some aspects, the imidazolium cations may enable surprisingly high total iodide concentrations in the reaction medium of, for example, from 20 to 35 wt. %, from 20 to 30 wt. % or from 20 to 25 wt. %. The imidazolium cation itself is preferably maintained in the reaction medium in an amount from 1.5 wt. % to 28 wt. %, e.g., from 2 to 23 wt. % or from 5 to 18 wt. %, based on the total weight of the reaction solution. In terms of lower limits, the concentration of the catalyst stabilizer(s)/co-promoter(s) in the reaction medium are preferably such that they maintain an iodide ion concentration in the reaction medium of at least 2 wt. %, at least 3 wt. %, at least 5 wt. %, at least 10 wt. %, at least 15 wt. %, at least 20 wt. %, at least 25 wt. %, or at least 30 wt. %, based on the total weight of the reaction medium. In terms of upper limits, the catalyst stabilizer(s)/co-promoter(s) in the reaction medium preferably are such that they maintain an iodide ion concentration of less than 35 wt. %, such as less than 30 wt. %, less than 25 wt. %, less than 20 wt. %, less than 15 wt. %, or less than 10 wt. %, based on the total weight of the reaction medium.

When the imidazolium iodide salt is maintained in combination with an inorganic iodide salt, such as lithium iodide, it is preferred that such salts are present in an amount sufficient to maintain the desired iodide concentration in the reaction solution. The relative ratios of the two components may vary widely. In one embodiment, for example, the molar ratio of imidazolium cation to alkali or alkaline earth metal cation in the reaction solution is maintained at from 1:100 to 100:1, e.g., from 1:50 to 50:1, from 1:10 to 10:1, from 1:3 to 1:1, or 1:2.

The stabilizing iodide co-promoter(s) may be maintained in the reaction medium at a total iodide ion to homogeneous catalyst (typically rhodium or iridium) molar ratio of 1:1 to 1000:1. In other embodiments, the total iodide concentration may be maintained in the reaction medium at a molar concentration of total iodide ion to rhodium/iridium of 25:1 to 950:1 or from 40:1 to 120:1. In still other embodiments, the total iodide concentration may be maintained in the reaction medium at a molar concentration of total iodide ion to rhodium/iridium from 60:1 to 100:1.

Generally, it is preferred that the imidazolium salt has a melting point that is below the temperature at which the carbonylation reaction is to be carried out. The melting point of the iodide salt depends, in part, upon the particular hydrocarbon groups ($R_1$ and $R_2$) that are bound to the imidazolium nitrogen atoms. In preferred embodiments, $R_1$ and $R_2$ are chosen so as to provide salts having low melting temperatures. To that end, the melting point of the iodide salt generally decreases as the number of carbon atoms that are present increases. The presence of a branched (versus straight-chained) structure also may lead to lower melting points.

In some embodiments, the imidazolium salt employed has a melting point of less than 170° C., e.g., less than 160° C., less than 155° C., less than 150° C., less than 145° C. or less than 140° C. In terms of lower limits, the imidazolium salt of the reaction medium may have a melting point of at least 10° C., at least 20° C., at least 50° C., at least 70° C., at least 100° C., at least 110° C., at least 125° C., or at least 140° C. In terms of ranges, the imidazolium salt of the reaction medium may have a melting point in the range of 10° C. to 170° C., e.g., from 20° C. to 160° C., from 40° C. to 160° C., from 50° C. to 155° C., from 100° C. to 150° C., or from 125° C. to 150° C. In one embodiment, the imidazolium salt is a liquid at room temperature (25° C.) and 1 atmosphere.

As noted above, of $R_1$ and $R_2$ should be different functional groups from one another. In one non-limiting embodiment, the imidazolium ion comprises an ion of the formula: $R_1R_2Im^+$, wherein $R_1$ is straight or branched butyl, hexyl, or octyl or cycloalkyl, and $R_2$ is methyl, ethyl, propyl, or straight or branched butyl, hexyl, octyl, decyl, dodecyl, tetradecyl or hexadecyl or cycloalkyl, with the proviso that $R_1$ and $R_2$ are different.

In some embodiments, the catalyst stabilizer/co-promoter is selected from the group consisting of ethylmethylimidazolium iodide, propylmethylimidazolium iodide, butylmethylimidazolium iodide, hexylmethylimidazolium iodide, octylmethylimidazolium iodide, cyclohexylmethylimidazolium iodide, propylethylimidazolium iodide, butylethylimidazolium iodide, hexylethylimidazolium iodide, octylethylimidazolium iodide, cyclohexylethylimidazolium iodide, and mixtures thereof. This listing is not exclusive and is not meant to limit the scope of the invention.

As indicated above, the specific imidazolium salt employed may vary widely so long as the imidazolium cation employed includes $R_1$ and $R_2$ functionality, as defined above. Additional exemplary, but not exclusive, imidazolium cations suitable for the imidazolium salts of the present invention are provided below in Table 1. It should be understood that independent of the specific counterion employed in the imidazolium salt that is added to the reaction medium, e.g., iodide or carboxylate (e.g., acetate) anion, the stabilizing imidazolium iodide form will be generated therein.

TABLE 1

Imidazolium Cations

| Name | $R_1$ | $R_2$ |
| --- | --- | --- |
| Ethylmethylimidazolium | Ethyl | Methyl |
| Propylmethylimidazolium | Propyl | Methyl |
| Butylmethylimidazolium | Butyl | Methyl |
| Hexylmethylimidazolium | Hexyl | Methyl |
| Octylmethylimidazolium | Octyl | Methyl |
| Decylmethylimidazolium | Decyl | Methyl |
| Cyclohexylmethylimidazolium | Cyclohexyl | Methyl |
| Propylethylimidazolium | Propyl | Ethyl |
| Butylethylimidazolium | Butyl | Ethyl |
| Hexylethylimidazolium | Hexyl | Ethyl |
| Octylethylimidazolium | Octyl | Ethyl |
| Decylethylimidazolium | Decyl | Ethyl |
| Cyclohexylethylimidazolium | Cyclohexyl | Ethyl |
| Ethylbutylimidazolium | Ethyl | Butyl |
| Propylbutylimidazolium | Propyl | Butyl |
| Hexylbutylimidazolium | Hexyl | Butyl |
| Octylbutylimidazolium | Octyl | Butyl |
| Decylbutylimidazolium | Decyl | Butyl |
| Cyclohexylbutylimidazolium | Cyclohexyl | Butyl |

Catalyst crystallization and precipitation can be a particular problem for reaction mediums at temperatures that are below typical reaction temperatures. Such lower temperatures may be encountered, for example, during reactor start up or shut down. Reaction mediums of the present invention, however, may be particularly resistant to catalyst crystallization and precipitation even at such low temperatures. Accordingly, in one embodiment, at least 99% of the homogeneous catalyst remains solubilized in the reaction medium when cooled to at least 25° C. or to at least 20° C.

To provide carbonylation reactions as described herein, all selected reaction medium components are dissolved or dispersed in the reaction medium vessel or reactor. During a period of active reaction, methanol and carbon monoxide are continuously fed to the reactor containing a reaction medium in which a desired partial pressure of carbon monoxide is maintained. The carbonylation reactor is typically a stirred autoclave within which the reacting liquid components are maintained at a constant level. Into the reactor, fresh methanol, sufficient water to maintain the desired concentration of water in the reaction medium, recycled catalyst solution from the flasher base, and typically recycled methyl iodide and methyl acetate from an overhead of the methyl iodide-acetic acid splitter column. In certain embodiments, the methyl acetate is maintained in the reaction medium at a concentration of from 0.5 wt. % to 30 wt. %, e.g., from 0.5 to 20 wt. % or from 0.5 to 10 wt. %. Alternate distillation systems can be employed so long as a means is provided for recovering the crude acetic acid and recycling to the reactor catalyst solution, methyl iodide, and methyl acetate. Carbon monoxide is continuously introduced into the reactor just below the agitator which is used to stir the contents. The carbon monoxide is thoroughly dispersed through the reaction medium. A gaseous purge stream is vented from the head of the reactor to prevent buildup of gaseous by-products and to maintain a set carbon monoxide partial pressure at a given total reactor pressure. The temperature of the reactor is controlled, and the carbon monoxide is introduced at a rate sufficient to maintain a constant total reactor pressure. The total reactor pressure is preferably from 1.5 MPa to 4.5 MPa absolute, with the reaction temperature typically maintained from 150° C. to 250° C.

Liquid product is drawn off the carbonylation reactor at a rate sufficient to maintain a constant level of the reaction medium and is introduced to a flasher unit. In the flasher unit, a catalyst solution is withdrawn as a base stream incorporating predominantly acetic acid containing rhodium/iridium catalyst, the iodide salt co-promoter, and the imidazolium stabilizer, along with lesser quantities of methyl acetate, the halogen promoter, and water. An overhead stream from the flasher comprises predominately product acetic acid along with methyl iodide, methyl acetate, and water. A portion of the carbon monoxide along with gaseous by-products such as methane, hydrogen, and carbon dioxide exit the top of the flasher. For additional information regarding acetic acid production systems and schemes, see U.S. Pat. No. 4,433,166 to Singleton et al.; U.S. Pat. No. 5,144,068 to Smith et al.; U.S. Pat. No. 6,677,480 to Huckman et al., and U.S. Pat. No. 7,053,241 to Torrence, each of which is incorporated herein by reference in its entirety. For more information regarding specific processes for producing acetic acid through carbonylation reactions, see the publication: Graub, M., Seidel, A., Torrence, P., Heymanns, P., Synthesis of Acetic Acid and Acetic Acid Anhydride from Methanol. Applied Homogeneous Catalysis with Organometallic Compounds. (1996), Volume 1, 104 138. Editor(s): Cornils, B., Herrmann, W., Publisher: VCH, Weinheim, Germany, which is incorporated herein by reference in its entirety.

As indicated above, the carbonylation system preferably is a homogeneous carbonylation system, meaning that the catalyst and reactor solution are preferably in the same phase, e.g., liquid phase. Embodiments of the inventive process described herein relate to the use of homogeneous catalyst systems, preferably homogenous rhodium-based or iridium-based catalyst systems.

A non-limiting exemplary carbonylation system is shown in appended FIG. 1. As shown, FIG. 1 includes a carbonylation unit 10 of the class preferably utilized in connection with the present invention. Unit 10 includes a reactor 12, a flasher 14, a light ends column 16, a drying or dehydration column 18 as well as optionally further purification, such as a heavy ends column to remove higher boiling impurities (not shown). Reactor 12 includes the reaction medium to which methanol and carbon monoxide are fed. A portion of the reaction medium is continuously provided to flasher 14 via line 22 where crude product is flashed and sent to light ends column 16 via line 24 as a hot vapor feed.

In column 16, the product is purified of light components which exit the column via line 26, are condensed in a first condenser 28 and then decanted in a decanter 30. Conventionally, the light phase from decanter 30 is refluxed to column 16 via line 32, while the heavy phase from decanter 30 is returned to the reactor via lines 34, 35. Also provided, but not shown, are absorbers and strippers used to recycle material into the system.

A purified product stream 40 is withdrawn as a (preferably liquid) side stream from column 16 and fed to drying column 18 where water is removed from the partially purified product. Product is withdrawn via line 42. If necessary, further purification may be done. The overhead and some product acetic acid is used as reflux for column 18 or recycled to the reactor via line 44. Column 16 generates a liquid residue stream 52 which is conventionally recycled with flasher residue to the reactor as shown.

In some embodiments, at least some of the raw materials (or reactor feed materials) for the above-described carbonylation process may be derived partially or entirely from syngas. For example, as described above, the acetic acid may be formed from methanol and carbon monoxide, both of which may be derived from syngas. For example, the methanol may be formed by steam reforming syngas, and the carbon monoxide may be separated from syngas. In other embodiments, the methanol may be formed in a carbon monoxide unit, e.g., as described in EP2076480; EP1923380; EP2072490; EP1914219; EP1904426; EP2072487; EO2072492; EP2072486; EP2060553; EP1741692; EP1907344; EP2060555; EP2186787; EP2072488; and U.S. Pat. No. 7,842,844, which are hereby incorporated by reference. Of course, this listing of methanol sources is merely exemplary and is not meant to be limiting. The syngas, in turn, may be derived from variety of carbon sources. The carbon source, for example, may be selected from the group consisting of natural gas, oil, petroleum, coal, biomass, and combinations thereof. The raw materials used in connection with the process of this invention may be derived from any suitable source including natural gas, petroleum, coal, biomass, and so forth.

As petroleum and natural gas prices fluctuate becoming either more or less expensive, methods for producing acetic acid intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. Accordingly, in some embodiments, some or all of the raw materials for the above-described carbonylation may be derived partially or entirely from syngas. For example, both the methanol and carbon monoxide may be derived from syngas. The syngas may be formed by partial oxidation reforming or steam reforming, and the carbon monoxide may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

Also, U.S. Pat. No. RE 35,377, incorporated herein by reference, discloses a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The acetic acid, in turn, may be hydrogenated to form ethanol and/or ethanol derivatives. Processes for hydrogenating acetic acid to form ethanol are described, for example, in U.S. Pat. Nos. 7,608,744; 7,863,489; US Publication Nos. US2010/0197985; US2011/0190547; US2011/0190548; US2011/027,5862; US2011/0282110; and in U.S. patent application Ser. Nos. 13/197,743; 13/197,738; 13/299,816, each of which is incorporated herein by reference in its entirety.

As discussed above, rhodium catalyst precipitation is frequently experienced in product recovery systems, especially flasher units. The benefits of the systems described herein in reducing rhodium catalyst precipitation are exemplified by the following experimental evaluations.

EXAMPLES

In Examples A-E and 1-5, except where otherwise indicated, various continuous carbonylation reactions were run at bench scale under the following conditions: 1000 wppm rhodium, 190° C., 30 bar CO, 2 wt. % water, 2 wt. % methyl acetate, and 10 wt. % methyl iodide. Observations as to crystallization and precipitation were made at start up and during the reaction run. Except where otherwise indicated, the reactions were run continuously for a maximum of 5-8 hours or were ended before this time period if catalyst crystallization or precipitation were observed. Experiments were repeated on a daily basis up to about 35 total hours unless precipitation or crystallization occurred. Examples A-E and 1-5 were run under continuous conditions in a small bench scale zirconium reactor. The unit was operated without a methyl iodide-acetic acid splitter column. A solution of methyl iodide, water, methyl acetate and methanol was fed continuously to the carbonylation reactor, and a flasher overhead crude product containing water, methyl iodide, methyl acetate and acetic acid was collected. This solution was analyzed to determine the methanol carbonylation rate, expressed as g-moles acetic acid/L of operating reactor volume/hr (STY). The methanol carbonylation rates obtained were compared to the CO consumed during the run, expressed as moles CO/L/hr. Rhodium stability was measured based on the amount of rhodium catalyst precipitation or crystallization in the reaction solution at operating conditions during the experiment.

Various examples were run with and without various imidazolium cations and with and without lithium iodide as a catalyst co-promoter/stabilizer as shown in Table 2 and at various total iodide loadings. Except for varying the total iodide concentrations in the reactor as inorganic iodide such as LiI and/or various imidazolium iodide salts, the reaction conditions were repeated in each of these examples to demonstrate the effect of imidazolium iodide salts on catalyst stability.

Comparative Examples A-D

Examples A-D were run with various iodide concentrations, and with all iodide being provided from lithium iodide. No imidazolium co-stabilizer was included. Experimental results are shown in Table 2 and reflect that catalyst stabilization was not achieved until iodide concentrations of 9.5 wt. % and greater.

Comparative Example E

Symmetric Imidazolium Iodide Salt 1,3-dimethylimidazolium iodide (MMImI) Example E was run with MMImI and with lithium iodide as a co-stabilizer. The result is shown in Table 2 and reflects that at an iodide concentration of 4.5 wt % as the symmetric imidazolium salt with an iodide concentration of 9.0 wt. % as lithium iodide (LiI) catalyst crystallization occurred during the continuous run which is reflected in the lower STY compared to Examples C-D.

Examples 1-3

Dissymmetric Imidazolium Iodide Salts

Examples 1-3 were conducted in which $R_1$ was methyl and $R_2$ was butyl, hexyl, or octyl substituents of the imidazolium iodide salt and with lithium iodide (LiI). The results are shown in Table 2 and clearly reflect that at identical iodide salt concentration distributions as in Comparative Example E, using a dissymmetric imidazolium iodide salt as the catalyst stabilizer in combination with lithium iodide as co-stabilizer complete rhodium catalyst stabilization is obtained as indicated by no precipitation or crystallization of the Rh catalyst during the run.

Examples 4-5

Dissymmetric Imidazolium Iodide Salt

Examples 4-5 were conducted in which $R_1$ was methyl and $R_2$ was butyl or hexyl substituents of the imidazolium iodide salt and without lithium iodide (LiI) as a co-stabilizer. The results are shown in Table 2 and significantly reflect the superior catalyst stabilization of a dissymmetric imidazolium iodide salt at as low an iodide concentration as 4.5 wt % compared to an inorganic iodide stabilizer at the same total iodide concentration demonstrated in Comparative Examples A-B.

These results clearly demonstrate a surprising and unexpected stabilizing effect of imidazolium cations of the form $R_1R_2Im^+$ as an iodide salt, wherein $R_1$ and $R_2$ are each independently a substituted or unsubstituted alkyl or cycloalkyl with the proviso that $R_1$ and $R_2$ are not the same. It is notable that the symmetric imidazolium salt Methylmethylimidazolium Iodide (MMImI) in Comparative Example E crystallized during the run.

TABLE 2

EXPERIMENTAL RESULTS

| Ex. | Component | $[I^-]_{ImI}$ (wt % iodide) | $[I^-]_{LiI}$ (wt % iodide) | Carb. Rates (mol/l/hr) | Precipitation (P)/ Crystallization (C) During Run |
|---|---|---|---|---|---|
| A | Rh/LiI | 0 | 4.5 | 15.5 | P |
| B | Rh/LiI | 0 | 6.5 | 16.5 | P |
| C | Rh/LiI | 0 | 9.5 | 17.5 | None |
| D | Rh/LiI | 0 | 14 | 17.3 | None |
| E | Rh/MMImI/LiI | 4.5 | 9.5 | 14.0 | C |
| 1 | Rh/BMImI/LiI | 4.5 | 9.5 | 17.0 | None |
| 2 | Rh/HexMImI/LiI | 4.5 | 9.5 | 17.5 | None |
| 3 | Rh/OctMImI/LiI | 4.5 | 9.5 | 17.0 | None |
| 4 | Rh/BMImI | 4.5 | 0 | 16.0 | None |
| 5 | Rh/HexMImI | 4.5 | 0 | 16.0 | None |

MMImI = Methylmethylimidazolium Iodide
BMImI = Butylmethylimidazolium Iodide
HexMImI = Hexylmethylimidazolium Iodide
OctMImI = Octylmethylimidazolium Iodide Examples F-G and 6-12

Extended Continuous Carbonylation

The continuous homogeneous reaction system employed contained (a) a liquid-phase carbonylation reactor, (b) a flasher, and (c) a methyl iodide-acetic acid splitter column. The carbonylation reactor was a stirred autoclave within which the reacting liquid contents were maintained automatically at a constant level. Into this reactor the following were continuously introduced: fresh methanol, recycled catalyst solution from the flasher base, and recycled methyl iodide, methyl acetate and water from the overhead of the methyl iodide-acetic acid splitter column. Water was maintained in the reaction medium at about 2 wt. %, methyl iodide was maintained at about 10 wt. % and methyl acetate was maintained at about 3.5 wt. %. The residue from the flasher was recirculated to the reactor. Carbon monoxide was continuously introduced into and thoroughly dispersed within the carbonylation reactor. A gaseous purge stream was vented from the head of the reactor to prevent buildup of gaseous by-product and to maintain a set carbon monoxide partial pressure at a given total reactor pressure.

Crude liquid product was drawn off from the carbonylation reactor at a rate sufficient to maintain a constant level therein and was introduced to the flasher at a point intermediate between the top and bottom thereof. In the flasher the catalyst solution was withdrawn as abuse stream predominantly containing acetic acid, the rhodium catalyst and the rhodium catalyst stabilizer iodide salts along with lesser quantities of methyl acetate, methyl iodide, and water, while the condensed overhead of the flasher comprised largely the crude product, acetic acid, along with methyl iodide, methyl acetate, and water. A portion of the carbon monoxide along with gaseous by-products such as methane, hydrogen, and carbon dioxide exited the top of the flasher.

The dry acetic acid (<1500 ppm water) product was drawn from the base of the methyl iodide-acetic acid splitter column for final purification as desired (although it can also be withdrawn as a side stream near the base). The overhead from the methyl iodide-acetic acid splitter, comprising mainly methyl iodide, methyl acetate and water, was recycled to the carbonylation reactor.

During the long continuous operating periods for these experiments, the rhodium stabilization (rhodium loss by precipitation of insoluble rhodium triiodide or crystallization of the rhodium catalyst in the flasher) was measured by the rate of decline in the rhodium concentration (ppm Rh/hr) in the reactor during extended operating periods in the continuous carbonylation system.

The dry acid from the base of the methyl iodide-acetic acid splitter column was collected to determine the methanol carbonylation rate, expressed as g-moles acetic acid/L of operating reactor volume/hr (STY). Rhodium stability was measured as the rate of loss of rhodium (ppm Rh/hr) in the reactor over time based on rhodium analysis of the reactor solution during the entire period of an experiment.

Figure 2:
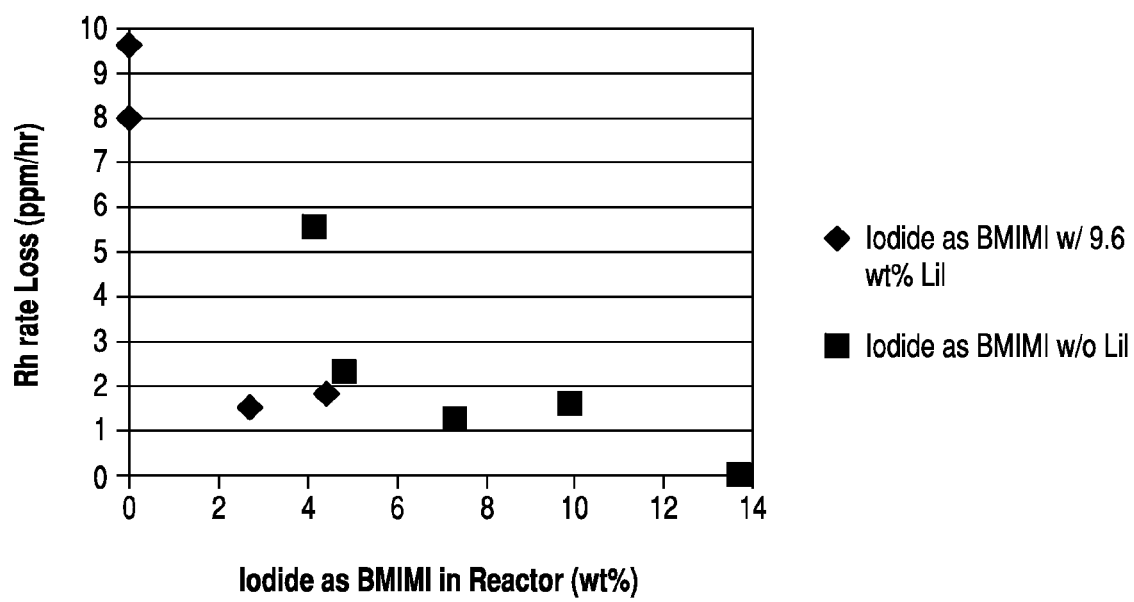
FIG. 2 is a chart summarizing rate of rhodium loss as a function of iodide concentration as BMImI in the reactor according to Examples F-G and 6-12.

Examples F-G and 6-12 were run under longer extended continuous conditions in a larger reactor than the previous examples without any interruptions in order to demonstrate the longer term thermal and chemical stability of the catalyst system with various dissymmetric imidazolium iodide salts with and without lithium iodide as a catalyst co-promoter/stabilizer at various total iodide loadings as shown in Table 3. Experimental results are summarized in FIG. 2. Except for varying the total iodide concentrations in the reactor as inorganic iodide such as LiI and/or various organic imidazolium iodide salts, the reaction conditions were repeated in each of these examples to demonstrate the effect of dissymmetric imidazolium iodide salts on catalyst stability.

In Examples F-G and 6-12, except where otherwise indicated, various continuous carbonylation reactions were run under the following conditions: 1000-1700 wppm rhodium, 202° C., 25-27 bar total pressure, 2-3 wt. % water, 3-4 wt. % methyl acetate, and 9-10 wt. % methyl iodide.

refer to another embodiment may be appropriately combined with other embodiments as will be appreciated by one of ordinary skill in the art. Furthermore, those of ordinary skill in the art will appreciate that the foregoing description is by way of example only, and is not intended to limit the invention.

We claim:

1. A process for producing acetic acid, the process comprising the steps of:
   reacting carbon monoxide with at least one reactant selected from the group consisting of methanol, methyl acetate, methyl formate, dimethyl ether and mixtures thereof in a reactor containing a reaction medium to produce a reaction product comprising acetic acid, wherein the reaction medium comprises a finite amount of water, a homogeneous catalyst, an alkyl halide promoter, and a catalyst stabilizer comprising a dissymmetric imidazolium cation $R_1R_2Im^+$ as an iodide salt, wherein $R_1$ and $R_2$ are each independently a substituted or unsubstituted alkyl or cycloalkyl, with the proviso that $R_1$ and $R_2$ are not the same; and
   maintaining the reaction medium at a total iodide ion concentration of from 2 to 35 wt. % and an alkyl halide promoter concentration of greater than 1 wt. %, based on the total weight of the reaction medium.

2. The process of claim 1, wherein the dissymmetric imidazolium cation is maintained in the reaction medium at a concentration of from 1.5 wt. % to 28 wt. %, based on the total weight of the reaction medium.

3. The process of claim 1, wherein the water concentration in the reaction medium is maintained at from 0.1 wt. % to 8 wt. %.

4. The process of claim 1, wherein the process has a carbonylation rate from 10 to 40 mol/l/hr.

5. The process of claim 1, wherein the process has a carbonylation rate from 15 to 20 mol/l/hr.

6. The process of claim 1, wherein the reaction medium is maintained at a total iodide ion to catalyst molar ratio of from 25:1 to 950:1.

7. The process of claim 1, wherein the reaction medium further comprises a metal iodide salt.

TABLE 3

EXPERIMENTAL RESULTS & REACTOR CONDITIONS

| Ex. | Component | Run Time (hrs) | Rh Loss Rate (ppm/hr) | Iodide as BMImI (wt %) | Iodide as LiI (wt %) | Iodide Total (wt %) | Rh (ppm) | HOAc STY (Mol/hr-L) |
|---|---|---|---|---|---|---|---|---|
| F | LiI | 44 | 8 | 0 | 9.6 | 9.6 | 1370 | 22.4 |
| 6 | BMImI | 136 | 1.5 | 2.7 | 9.7 | 12.4 | 1124 | 20.9 |
| G | LiI | 28 | 9.6 | 0 | 9.6 | 9.6 | 1343 | 18.2 |
| 7 | BMImI | 167 | 1.8 | 4.4 | 9.6 | 14 | 1081 | 17.2 |
| 8 | BMImI | 84 | 5.5 | 4.2 | 0 | 4.2 | 1145 | 21.9 |
| 9 | BMImI | 84 | 2.3 | 4.8 | 0 | 4.8 | 1134 | 21.9 |
| 10 | BMImI | 126 | 1.2 | 7.3 | 0 | 7.3 | 1246 | 23.7 |
| 11 | BMImI | 102 | 1.6 | 9.9 | 0 | 9.9 | 1313 | 26.2 |
| 12 | BMImI | 136 | 0 | 13.7 | 0 | 13.7 | 1628 | 28.2 |

While the invention has been described in detail, modifications within the spirit and scope of the invention will be readily apparent to those of skill in the art. It should be understood that aspects of the invention and portions of various embodiments and various features recited above and/or in the appended claims may be combined or interchanged either in whole or in part. In the foregoing descriptions of the various embodiments, those embodiments which 8. The process of claim 1, wherein the reaction medium further comprises an alkali or alkaline earth metal iodide salt at an imidazolium to alkali or alkaline earth metal molar ratio of from 1:10 to 10:1.

9. The process of claim 1, wherein the homogeneous catalyst comprises rhodium.

10. The process of claim 1, wherein at least 99 % of the homogeneous catalyst remains solubilized in the reaction medium when cooled to at least 20° C.

11. The process of claim 1, wherein the alkyl halide promoter is maintained in the reaction medium at a concentration greater than 5 wt. %.

12. The process of claim 1, wherein the reaction medium further comprises methyl acetate, the process further comprising the step of maintaining the reaction medium at a methyl acetate concentration from 0.5 to 20 wt. %, based on the total weight of the reaction medium.

13. The process of claim 1, wherein the reaction medium further comprises methyl acetate, the process further comprising the step of maintaining the reaction medium at a methyl acetate concentration from 0.5 to 10 wt. %, based on the total weight of the reaction medium.

14. The process of claim 1, wherein the reaction medium is maintained at a total iodide concentration from 3 to 35 wt. %.

15. The process of claim 1, wherein the catalyst stabilizer has a melting point of less than 170° C.

16. The process of claim 1, wherein the catalyst stabilizer is a liquid at 25° C.

17. The process of claim 1, wherein $R_1$ is selected from ethyl, butyl, hexyl and octyl and $R_2$ is methyl.

18. The process of claim 1, wherein the catalyst stabilizer comprises butyl methyl imidazolium ion.

19. The process of claim 1, wherein the catalyst stabilizer comprises hexyl methyl imidazolium ion.

20. The process of claim 1, wherein the catalyst stabilizer comprises octyl methyl imidazolium ion.

\* \* \* \* \*